United States Patent [19]

Pidorenko

[11] Patent Number: 4,787,396

[45] Date of Patent: Nov. 29, 1988

[54] FIBEROPTIC PRESSURE TRANSDUCER

[75] Inventor: John Pidorenko, Ypsilanti, Mich.

[73] Assignee: Fiberoptic Sensor Technologies, Inc., Ann Arbor, Mich.

[21] Appl. No.: 63,411

[22] Filed: Jun. 18, 1987

[51] Int. Cl.$^4$ ................................................. A61B 5/02
[52] U.S. Cl. ..................................... 128/667; 128/675; 128/748; 73/705
[58] Field of Search ........................... 128/644–647, 128/672–673, 675, 748, 634; 73/705, 708, 715

[56] References Cited

U.S. PATENT DOCUMENTS

| | | | |
|---|---|---|---|
| 3,267,932 | 8/1966 | Valliere | 128/675 |
| 4,201,222 | 5/1980 | Haase | 128/673 X |
| 4,210,029 | 7/1980 | Porter | 128/748 X |
| 4,286,585 | 9/1981 | Ogawa | 128/772 X |
| 4,487,206 | 12/1984 | Aagard | 128/667 |
| 4,494,550 | 1/1985 | Blazek et al. | 128/666 X |
| 4,543,961 | 10/1985 | Brown | 128/675 X |
| 4,554,927 | 11/1985 | Fussell | 128/673 X |
| 4,593,701 | 6/1986 | Kobayashi et al. | 128/673 X |
| 4,691,709 | 9/1987 | Cohen | 128/667 |
| 4,703,757 | 11/1987 | Cohen | 128/667 |
| 4,711,246 | 12/1987 | Alderson | 128/667 |

*Primary Examiner*—Edward M. Coven
*Assistant Examiner*—Angela D. Sykes
*Attorney, Agent, or Firm*—Charles S. McGuire

[57] ABSTRACT

A miniaturized pressure transducer, particularly suited for intravascular blood pressure measurement, utilizing a single optical fiber for transmitting light both to and from a flexible diaphragm having a light-reflecting surface on one side, the opposite side being exposed to and deflected in accordance with the pressure being measured. The end of the fiber through which light is transmitted to and reflected light received from the diaphragm is ground to form a spherical lens integral with the fiber, whereby light passing through the end of the fiber is focused at a predetermined focal point. The fiber is axially positioned so that the center of the diaphragm, which coincides with the lens axis, is at the focal point when the diaphragm is at maximum deflection, i.e., when its opposite surface is exposed to a predetermined, maximum anticipated pressure.

12 Claims, 4 Drawing Sheets

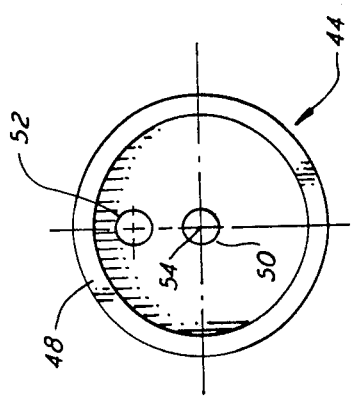
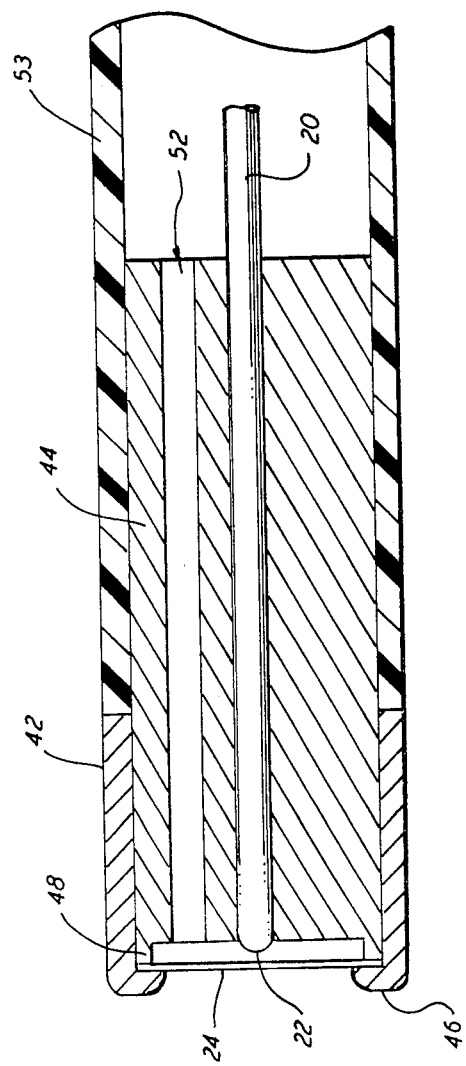

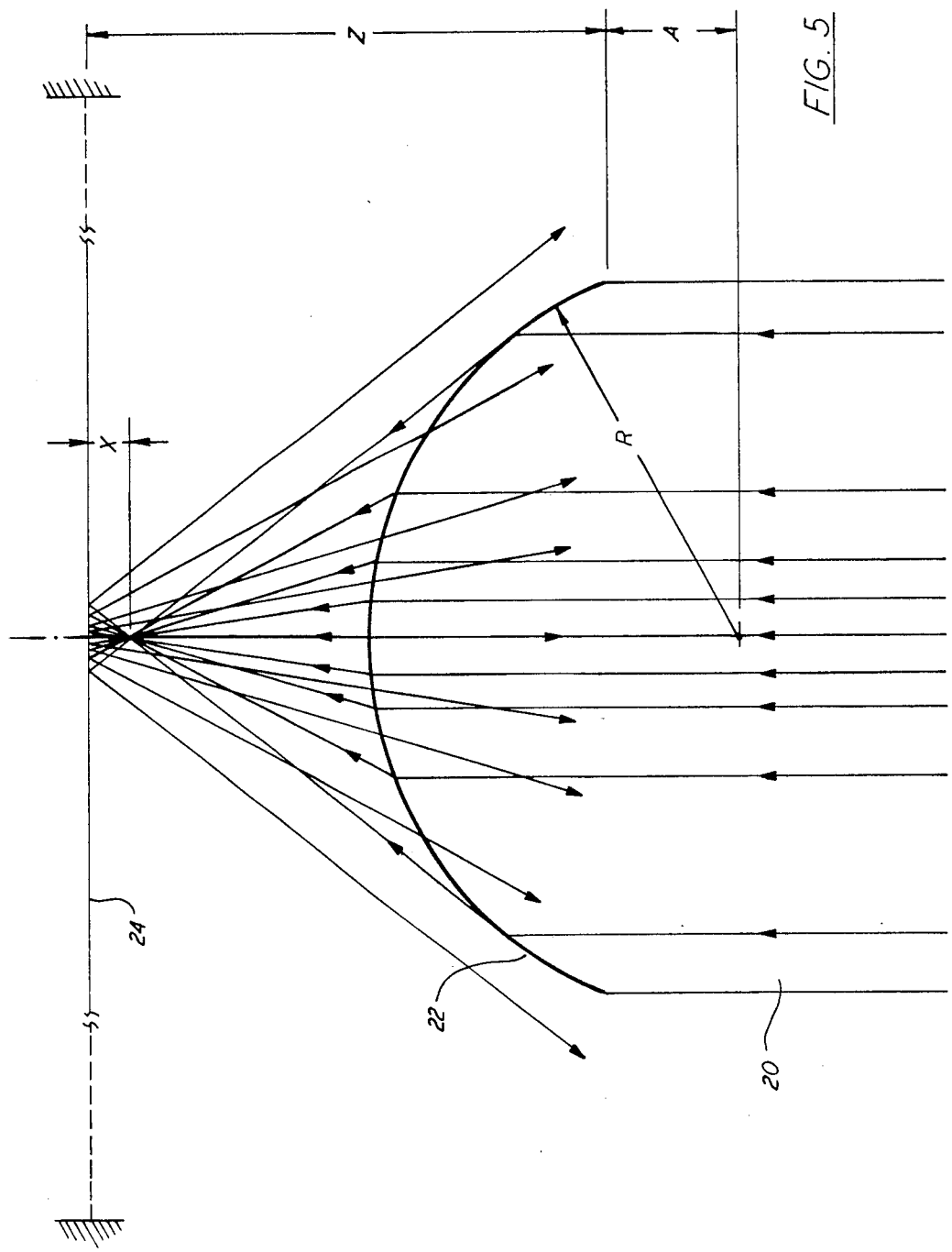

FIBEROPTIC PRESSURE TRANSDUCER

BACKGROUND OF THE INVENTION

The present invention relates to fiber optic coupled pressure transducers and, more specifically, to miniaturized pressure measurement apparatus, such as intravascular catheter tip fiber optic pressure sensors.

Measurement of intravascular blood pressure by means of a hollow catheter tube filled with saline solution and attached to an external transducer has been largely supplanted by fiber optic coupled catheter tips incorporating a pressure transducer. The prior art encompassing the latter includes fiber optic pressure sensors in which a light-reflecting, pressure-deformable diaphragm at the end of the catheter tip is spaced a small distance from the end of one or more fibers and modulates the light reflected back through the fibers in accordance with the pressure responsive position of the diaphragm. The present invention is concerned with pressure sensing apparatus of this type which employs a single fiber both for transmitting light to the diaphragm and for carrying the reflected light back to sensing apparatus.

In copending application Ser. No. 902,666, filed Sept. 2, 1986, now U.S. Pat. No. 4,711,246 there is disclosed a single fiber pressure transducer which simulates the function of a fiber bundle by having the fiber end adjacent the diaphragm covered by a light-absorptive coating with a plurality of discrete, light-transmitting openings. A second type of single fiber optical pressure measuring apparatus is described in abandoned application Ser. No. 298,972, referenced in U.S. Pat. No. 4,487,206, the latter relating to a three-fiber embodiment. The single fiber of the abandoned application, as well as the three fibers of the patented embodiment, are bonded to a molded plastic optical lens with a spherically curved surface which focuses the transmitted light on the diaphragm. In both embodiments, the lens has a diameter essentially equal to that of the diaphragm.

The present invention is directed to improvements in single fiber optical pressure transducers wherein light transmitted through the fiber is focused on the deformable, reflecting diaphragm. Objects of the invention are to effect economies in the manufacture of such apparatus and to improve the sensitivity of the device.

Other objects will in part be obvious and will in part appear hereinafter.

SUMMARY OF THE INVENTION

In furtherance of the foregoing objects, the invention contemplates a miniaturized, pressure-sensing tip, suitable for use in measurement of intravascular blood pressure, wherein a circular diaphragm is engaged about its periphery between a cap and a ferrule which are press fit in permanent engagement. Two passageways extend through the ferrule parallel to its axis and perpendicular to the plane of the diaphragm when undistorted. A single optical fiber is inserted into one of the passageways and, after being properly axially positioned, is permanently secured to the ferrule by a cement which is applied to the fiber as it is inserted.

The end of the fiber which is held by the ferrule in predetermined spacing from the diaphragm is ground to form a convex surface with a predetermined radius. The radius is related to the position of the diaphragm as deflected by a predetermined pressure differential, which is a function of the thickness and diameter of the diaphragm. The second passageway is used for venting purposes to insure that the surface of the diaphragm facing the end of the fiber is always at atmospheric, or other known, constant pressure as the opposite surface is exposed to the pressure to be measured.

Light passes out through the lens on the end of the fiber in a cone-shaped pattern and is reflected by the diaphragm, being modulated in intensity as a function of diaphragm position, as determined by the pressure being measured. Thus, it is unnecessary to provide a separate lens element to which the fiber is bonded. Sensitivity of the measurements is increased by properly relating the radius of the lens on the fiber end to the deflection rate of the diaphragm.

Design of the pressure transducer permits assembly in a rapid and efficient manner, thereby reducing fabrication costs, the preferred steps in the assembly procedure also being described more fully later herein.

BRIEF DESCRIPTION OF THE DRAWINGS

FIG. 2 is an enlarged, side elevational view, in section, of portions of the apparatus of FIG. 1;

FIG. 3 is an end view of one of the elements of the apparatus; and

FIGS. 4 and 5 are diagrams illustrating the operating principles and performance of the apparatus.

DETAILED DESCRIPTION

Figure 1:
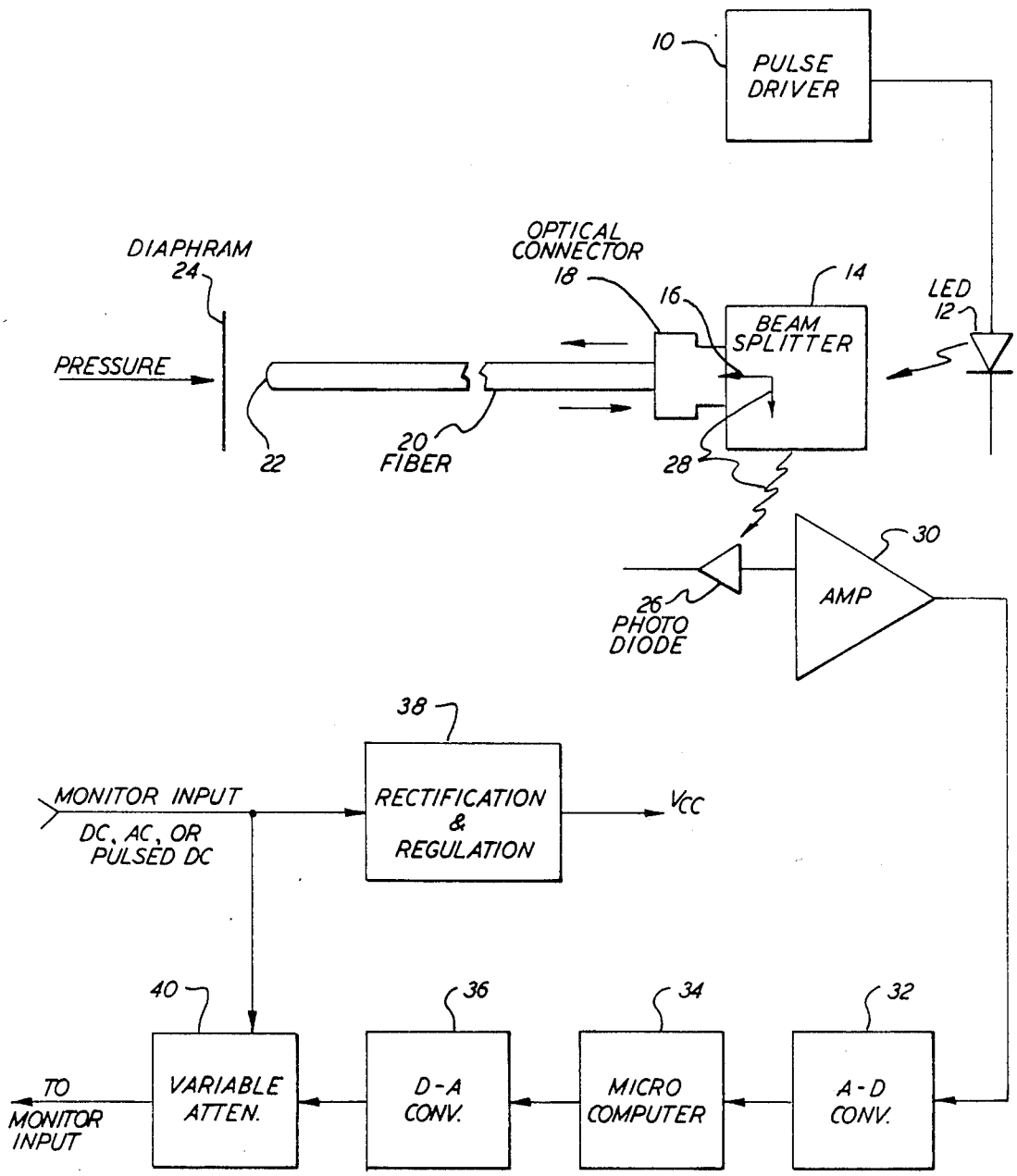
FIG. 1 is a somewhat diagrammatic illustration of pressure measuring apparatus embodying the present invention.

Referring now to FIG. 1, pulse generator 10 drives light emitting diode (LED) 12 to generate short pulses of very high intensity light, in conventional fashion. The light pulses passing through beam splitter 14, indicated by arrow 16, pass through optical connector 18 and travel along optical fiber 20. The light rays which exit end 22 of fiber 20 are reflected by flexible diaphragm 24 and, depending upon the angle of reflection, either pass back into fiber 20 or are "lost," i.e., reflected outside the fiber end. As explained later in more detail, the amount of light reflected back into fiber 20 is a function of the distance between fiber end 22 and the reflecting surface of diaphragm 24. As also explained later, fiber end 22 is formed with a radius, providing a spherical lens which focuses light at a predetermined position relative to the reflecting surface of diaphragm 24. A portion of the light passing back through fiber 20 is reflected by beam splitter 14 and impinges upon photo diode 26, such light being indicated by arrow 28. The resulting electrical signal from photo diode 26, as modulated by the intensity of light from beam splitter 14 impinging thereon, is amplified by amplifier 30, and converted to a digital signal by A to D converter 32. The digital signal is then processed for linearity and other functions by microcomputer 34 in conventional fashion, and converted back to an analog signal by D to A converter 36.

Monitors for pressure transducers of the type with which the present invention is concerned supply excitation voltage which may be AC, DC, or pulsed DC. The unit will further have a back-up battery power supply which is rechargeable, in the vent that the monitor's excitation voltage is inadequate to power the unit. However, where excitation voltage is adequate, power from the monitor is rectified and regulated by appropriate circuitry, indicated by block 38, to supply the operating power for the system electronics, indicated as Vcc. Monitor power is also supplied to variable attenuator 40, as is the output of D to A converter 36. The signal output of variable attenuator 40, supplied to the monitor input, is a direct representation of the excitation waveform. Thus, the signal becomes compatible with all or most monitors.

Turning now to FIG. 2, a preferred embodiment of the pressure transducer tip of the invention, suitable for use in catheter application, is shown. The tip includes hollow cylindrical cap 42, ferrule 44, and previously mentioned diaphragm 24, the latter being permanently affixed between lip 46 on cap 42 and annular shoulder 48 on the end of ferrule 44. Cap 42 and ferrule 44 are both fabricated from high yield, grade 4 titanium, a material which is accepted in the medical field and has excellent mechanical properties for application as a pressure transducer catheter tip. Cap 42 is formed from titanium rod, drilled to the inside diameter of lip 46 and then bored to provide a step for the diaphragm. It is then cut to appropriate length, deburred, cleaned, polished and a radius formed at both sides of lip 46.

Ferrule 44 is preferably formed from continuous, cylindrical, drawn tubing which is fed through a screw machine where it is turned, a step is cut in the end to provide annular shoulder 48, and then cut to length. The preferred method of fabricating radius 22 on the end of fiber 20 is to place it into a lapping jig where a lapping stone automatically grinds a radius of desired dimension. Although the optical fibers used in such applications are small, e.g., 0.010" in diameter, the radius may be ground on the end by conventional techniques.

The fabrication of ferrule 44 includes the drilling of two passageways parallel to the axis thereof. One of the openings, indicated in FIG. 3 by reference numeral 50, is used for passage of fiber 20 through the ferrule and is drilled to a nominal diamter very close to the diameter of the fiber. The other passageway 52 provides a vent opening for equalizing the pressure at both ends of the ferrule. The pressure may be established at a desired value for calibration purposes by connecting a vacuum pump and relief valve to tubing 53 at a convenient location and measuring the pressure by a silicon diaphragm, high accuracy, pressure transducer, as disclosed in previously mentioned application Ser. No. 902,666. The central axis of ferrule 44 is indicated at 54 in FIG. 3. In the disclosed embodiment, the central axis of fiber 20, as defined by the axis of passageway 50, coincides with ferrule axis 54 which passes through the center of diaphragm 24 in the assembled condition of the transducer tip. In some applications, it may be desirable to place the fiber axis at a position other than the center of the diaphragm. Passageway 52 may be of the same nominal diameter as passageway 50, i.e., 0.010".

Figure 4:
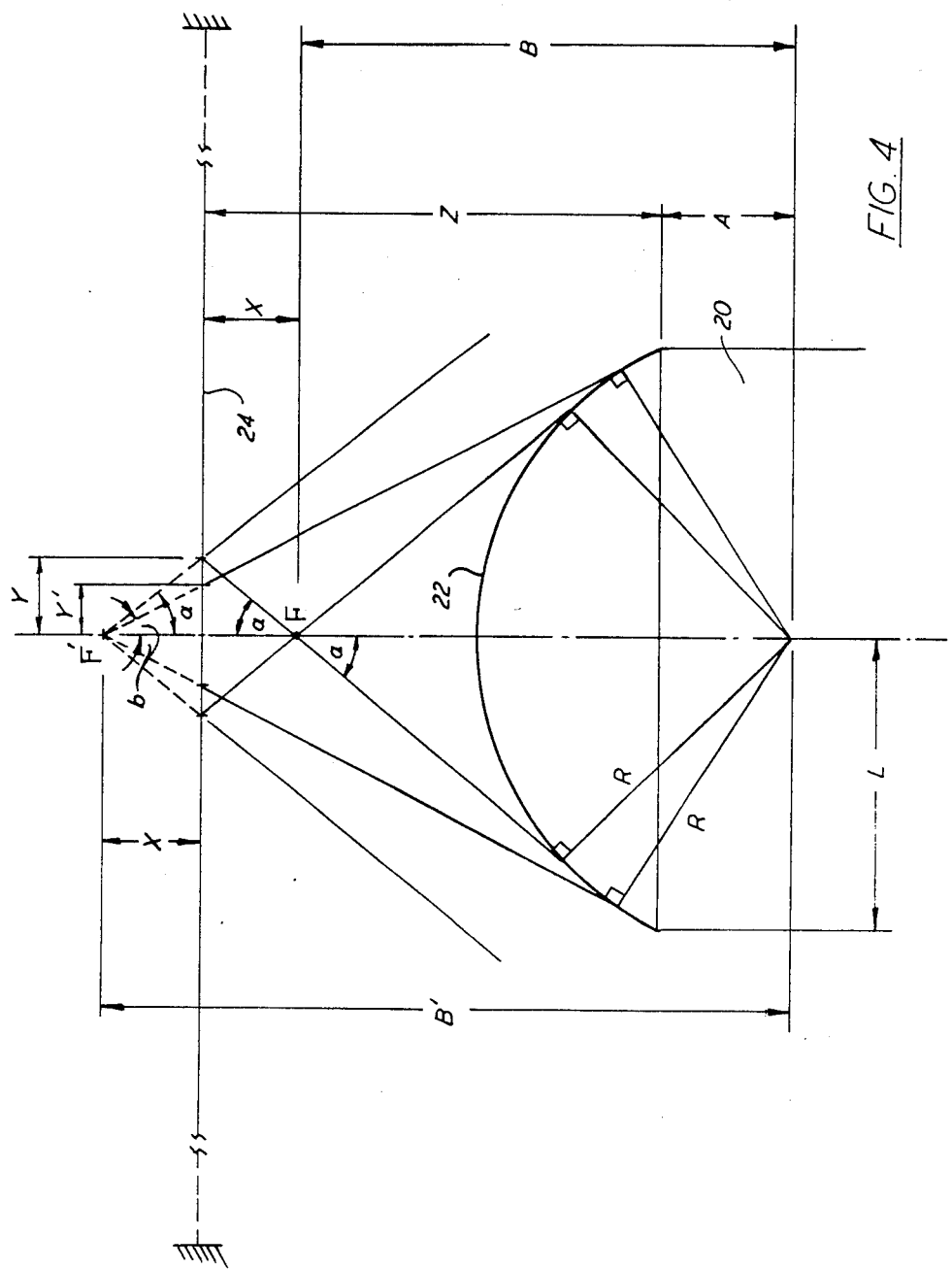

Referring now to the diagram of FIGS. 4 and 5, wherein upper and lower case letters denote linear dimensions and lower case letters angles, respectively, diaphragm 24 is shown in the flat or undeflected position, i.e., with equal pressure on opposite sides of the diaphragm. Fiber 20 is axially spaced from diaphragm 24 by the distance necessary to place the diaphragm surface at the focal point F of lens 22 when the diaphragm is at the maximum anticipated deflection, e.g., at a gauge pressure of 350 mm Hg. Therefore, diaphragm 24 in its undeflected position is spaced from focal point F by a distance denoted by the letter X. The light transmitted through lens 22 which impinges on diaphragm 24 is represented by a circle having a radius Y; that is, all light rays transmitted within lines tangent to the surface of lens 22 passing through focal point F will impinge on the surface of diaphragm 24, as may be seen from FIGS. 4 and 5.

Since diaphragm 24, in its undeflected position, is spaced from focal point F by a distance X, some of the light impinging on the diaphragm will be reflected back to lens 22 and some will be reflected outside the lens, i.e., will be "lost". The amount of light reflected back to the lens is represented by a circle having a radius Y'; that is, all light rays reflected within lines tangent to the surface of lens 22 and passing through point F', a point on the lens axis on the opposite side of diaphragm 24 from focal point F and spaced an equal distance (X) from the diaphragm surface. Thus, the amount of light lost at zero diaphragm deflection may be expressed as the difference in areas between circles of radius Y and Y'. This calculation may be made from the known dimensions of the radii of fiber 20 (L) and lens 22 (R), the axial spacing Z of the end of fiber 20 from diaphragm 24, and maximum diaphragm deflection X, which is a function of the material and physical dimensions (thickness and diameter) of diaphragm 24. A sample calculation of the percentage of light lost for a fiber having a radius L of 0.005", a lens having a radius R of 0.00535272", a linear dimension Z of 0.00744" and a diaphragm having a maximum deflection X (the diaphragm surface when flat being spaced from focal point F of the lens by distance X) of 0.000582", is as follows:

$$A = \sqrt{R^2 - L^2} = \sqrt{0.00535272^2 - 0.005^2} = 1.9109189 \times 10^{-3}$$

$$B = Z - X + A = 8.7927189 \times 10^{-3}$$

$$\sin a = R/B \quad a = \sin^{-1}(R/B) = \sin^{-1}(0.00535272/0.0087927189)$$
$$= 37.500426°$$

$$Y/X = \tan a \quad Y = X \tan a = 0.0005582 \times \tan(37.500426°)$$
$$= 4.2832852 \times 10^{-4}$$

$$B' = B + 2X = 8.7927189 \times 10^{-3} + 2(0.0005582) = 9.9091189 \times 10^3$$

$$\sin c = R/B' \quad c = \sin^{-1}(R/B') = \sin^{-1}(0.00535272/9.9091189 \times 10^{-3})$$
$$= 32.695977°$$

$$Y'/X = \tan c \quad Y' = X \tan c = 0.0005582 \times \tan(32.695977°)$$
$$= 3.5830268 \times 10^{-4}$$

$\pi Y^2$ = The total area of light which hits the diaphragm $\pi Y'^2$ = The area of light which reflects to the fiber The area loss = $\pi Y^2 - \pi Y'^2$ $$\text{Loss percentage} = \pi(Y^2 - Y'^2)/\pi Y^2$$
$$= 1 - \left(\frac{Y'}{Y}\right)^2 = 1 - \left(\frac{3.5830268 \times 10^{-4}}{4.2832852 \times 10^{-4}}\right)^2$$
$$= 0.3002448 = 30\%$$

FIG. 5 illustrates diagrammatically the light rays transmitted to and reflected by diaphragm 24 with the elements of FIG. 4 positioned as shown therein. Although FIG. 4 is exaggerated for purposes of illustration, FIG. 5 is substantially to scale, magnified 500 times. When diaphragm 24 is at its fully deflected position in FIGS. 4 and 5, i.e., when the center of the diaphragm is at point F, essentially all of the light transmitted to the diaphragm surface will be reflected back to lens 22 and will pass back through fiber 20. Thus, the amount of light reflected back through the fiber at zero deflection of the diaphragm is approximately 70% of that reflected at maximum deflection (100%–30%). The pressure exerted on the diaphragm between zero and maximum may thus be determined from the intensity of reflected light an an extremely compact device of relatively simple and inexpensive construction.

What is claimed is:

1. A fiber optic pressure transducer comprising:
   (a) light generating means;
   (b) an elongated, optical fiber having a first terminal end positioned to receive light from said generating means and a second terminal end to which said light is carried through said fiber;
   (c) a deformable member having a first, light reflecting surface positioned in opposed, spaced relation to said second terminal end and movable with respect thereto in accordance with the pressure exerted on the side of said deformable member opposite said first surface;
   (d) a spherical lens formed integrally as a radius on said second terminal end and having a focal point positioned in predetermined relationship to said light reflecting surface, whereby light carried from said first to said second end of said fiber passes through said lens and impinges on said light reflecting surface and at least a portion of said light reflected by said surface passes back through said lens and fiber and out of said first end thereof; and
   (e) means for generating an electrical signal commensurate with the intensity of light passing out of said first end, said intensity being a function of the distance between said lens and said light reflecting surface and thereby of said pressure exerted on said opposite side of said deformable member.

2. The invention according to claim 1 wherein said deformable member comprises a circular diaphragm fixedly engaged about its periphery, whereby pressure exerted on said opposite side produces the greatest deflection at the center of said diaphragm.

3. The invention according to claim 2 wherein the optical axis of said lens is coincident with the center of said diaphragm.

4. The invention according to claim 1 wherein said means for generating an electrical signal comprises a photo diode arranged to receive said light carried back through said fiber.

5. The invention according to claim 4 and further comprising a hollow, flexible tube through which said fiber extends.

6. The invention according to claim 5 and further including a hollow cap engaged with said tube to enclose said second terminal end of said fiber.

7. The invention according to claim 6 wherein said deformable member comprises an end closure of said cap.

8. The invention according to claim 7 wherein said end closure comprises a circular diaphragm fixedly engaged about its periphery, whereby pressure exerted on said opposite side produces the greatest deflection at the center of said diaphragm.

9. The invention according to claim 1 wherein said deformable member is movable from an undeflected position toward said lens to a maximum deflected position.

10. The invention according to claim 9 wherein the point on said reflecting surface intersected by the optical axis of said lens is spaced from said lens by a distance substantially equal to the focal length of said lens when said deformable member is in said maximum deflected position.

11. The invention according to claim 10 wherein said deformable member comprises a circular diaphragm fixedly engaged about its periphery, whereby pressure exerted on said opposite side produces the greatest deflection at the center of said diaphragm.

12. The invention according to claim 11 wherein the optical axis of said lens is coincident with the center of said diaphragm.

* * * * *